United States Patent [19]

Nishimura

[11] Patent Number: 5,144,058
[45] Date of Patent: Sep. 1, 1992

[54] COLORLESS GRAINED ALPHA-FORM CRYSTALS OF TETRAKIS [3-(3,5-DI-T-BUTYL-4-HYDROXYPHENYL)-PROPIONYLOXYMETHYL]METHANE AND PROCESS FOR ITS MANUFACTURE

[75] Inventor: Atsushi Nishimura, Saitama, Japan

[73] Assignee: International Chemical Consultant, Ltd., Japan

[21] Appl. No.: 538,818

[22] Filed: Jun. 15, 1990

[30] Foreign Application Priority Data

Mar. 30, 1990 [JP] Japan ................................. 2-83124

[51] Int. Cl.$^5$ ............................................. C07C 69/76
[52] U.S. Cl. ............................................. 560/75; 560/67
[58] Field of Search ............................. 560/75, 67

[56] References Cited

U.S. PATENT DOCUMENTS

| | | | |
|---|---|---|---|
| 3,644,482 | 2/1972 | Dexter et al. | 560/75 |
| 4,405,807 | 9/1980 | Hasui | 560/75 |
| 4,594,444 | 6/1986 | Orban | 560/67 |
| 4,739,102 | 4/1988 | Tokunaga . | |

*Primary Examiner*—Paul J. Killos
*Attorney, Agent, or Firm*—Lowe, Price, LeBlanc & Becker

[57] ABSTRACT

Tetrakis[3-(3,5-di-t-butyl-4-hydroxyphenyl)propionyloxymethyl]methane in the form of grained alpha-form crystals having improved coloration. The above compound is prepared by transesterifying low-alkyl 3-(3,5-di-t-butyl-4-hydroxyphenyl)propionate with pentaerythritol in the presence of catalyst and aliphatic hydrocarbons as reaction solvent.

12 Claims, No Drawings

COLORLESS GRAINED ALPHA-FORM CRYSTALS OF TETRAKIS [3-(3,5-DI-T-BUTYL-4-HYDROXYPHENYL)PROPIONYLOXYMETHYL]METHANE AND PROCESS FOR ITS MANUFACTURE

BACKGROUND OF THE INVENTION

This invention relates to tetrakis[3-(3,5-di-t-butyl-4-hydroxyphenyl)propionyloxymethyl]methane [hereinafter called compound (1)] in the grained alpha-form crystals having improved coloration, and a process for the production thereof.

Compound (1) is disclosed e.g. in U.S. Pat. No. 3,644,482 and has been accepted as excellent anti-deterioration agent against heat and oxidation for organic material such as synthetic polymers like polyolefines, polyesters, polystyrenes, polyurethanes, polyvinyl chlorides, etc. With a recent wide use of these synthetic polymers as durable consumer goods such as automobiles and electric appliances, demand for higher qualities of additives for plastics is growing. Especially, the colorlessness of such stabilizing agents is essential since coloration of final plastic products is degraded by the use of colored agents. And also, demand for powder-free additives is increasing from the industrial viewpoint of handleability, transportability, flowability, etc. The compound (1) available on the market is, however, a little colored or in the form of powder or aggregate of fine crystals having a low mechanical strength to be crushed during handling, storage and/or transportation, resulting in low bulk density, inferior fluidity and easy scattering.

According to U.S. Pat. No. 3,644,482, Compound (1) is prepared by transesterifying low-alkyl 3-(3,5-di-t-butyl-4-hydroxyphenyl)propionate [hereinafter called compound (2)] with pentaerythritol in the presence of alkali metal hydride as catalyst and absence of reaction solvent or presence of dimethylsulfoxide, followed by the recrystallization from isopropanol or n-hexane. The compound (1) obtained by the above method is, as described in U.S. Pat. No. 4,405,807 colored yellow and can not be supplied to the market.

Japanese Pat. No. 13018/60 (corresponding to U.S. Pat. No. 4,405,807) states that compound (1) is obtained by reacting compound (2) with pentaerythritol in the presence of alkali metal methoxide and dimethylformamide with removal of the formed low alcohol under reduced pressure, adding isopropanol to isolate a molecular adduct compound of the compound (1) and isopropanol, and subsequently recrystallizing it from ethanol and/or methanol. The patent also refers to dimethyl sulfoxide, dimethyl formamide, tetrahydrofuran, dioxane, diglyme, dimethyl acetamide, hexamethyl phosphoramide, 1,2-dimethoxyethane, acetonitrile, propionitrile and t-butyl alcohol, which are all polar solvents, as examples of usable reaction solvents; and refers to alkali or alkaline earth metal halides, lower alcoxides of alkali metals, and metallic sodium and metallic potassium, which are derivatives of either alkali metals or alkaline earth metals, as examples of usable catalysts.

U.S. Pat. No. 4,739,102 discloses a process for the production of compound (1) in the beta-form of crystals, where the compound (1) is prepared by reacting compound (2) with pentaerythritol with removal of the formed low alcohol under reduced pressure, in the presence of alkali metal amide or other alkali or alkaline earth metal derivatives as catalyst and a small amount of aromatic hydrocarbon solvent like tetraline or other polar solvents, distilling off the solvent under reduced pressure, and then recrystallizing the product from a mixture of methanol and/or ethanol and water.

The above proposed processes for the manufacture of compound (1) have been developed only by modifications of recrystallization procedures, due to the difficulty in completion of the transesterification reaction without formation of colored by-products which are difficult to be removed by the recrystallization from aliphatic hydrocarbons. By reason of decoloration, the compound (1) has been recrystallized from low alcohol such as methanol, ethanol or a mixture of it and water. The use of such polar solvent as recrystallization solvent is effective on removal of colored matter from the compound (1). The crystals obtained by the recrystallization are, however, in the form of powder or aggregate of fine crystals with unfavorable characters such as low fluidity and low mechanical strength.

In the conventional transesterification processes for the production of compound (1), a polar solvent is used as reaction solvent. As the starting material, pentaerythritol, has an exceedingly high polarity and high melting point of 261° to 262° C., the use of polar solvents is effective to dissolve the said starting material. Such solvents, however, have not brought about a positive effect on lowering the formation of colored by-products, but rather made it difficult to complete the transesterification reaction, resulting in prolonged reaction time or less conversion.

Compound (1) has been known, as disclosed in U.S. Pat. No. 4,405,807, to have 5 crystal forms, i.e. alpha-form, beta-form, gamma-form, delta-form and lambda-form. The compound (1) widely available on the market has a crystal structure of beta-form having the melting point of 113° to 115° C. However, the said form crystals are, as described in U.S. Pat. No. 4,739,102, substantially an aggregate of fine crystals, which leads to be readily crushed and reform agglomerates.

According to U.S. Pat. No. 4,405,807 and 4,739,102, alpha-form crystals of compound (1) are obtained by the recrystallization from hexane or heptane; and the said crystals are in the shape of granules or grains having the melting point of 120° to 125° C., which is higher than that of beta-form. Although physical properties of alphaform crystals are superior to those of beta-form, the former crystals obtained by the conventional transesterification methods are, as described in U.S. Pat. No. 4,405,807, colored yellow and have not been supplied to the market.

The purpose of the present invention is to provide a new transesterification process in which compound (1) is manufactured without coloration. The new process found has surprisingly decreased the formation of colored by-products, by the use of aliphatic hydrocarbons as reaction solvent having the high boiling point of 100° to 300° C., preferably 155° to 205° C. Such improved process of transesterification have made it possible to obtain compound (1) in the form of colorless grained alpha-form crystals by simple crystallization from aliphatic hydrocarbons; and additionally, very little formation of by-products have made the grain size of crystals to be larger. And also, the use of organo-tin compounds as catalyst together with the said aliphatic hydrocarbon solvent increases the colorlessness of crystals. Furthermore, a much whiter compound (1) is obtainable by the direct crystallization from the reaction mixture without the step of reduced-pressure stripping. This also simplifys the manufacturing process of compound (1), producing an industrially beneficial effect.

SUMMARY OF THE INVENTION

In accordance with the present invention, tetrakis[3-(3,5-di-t-butyl-4-hydroxyphenyl)propionyloxymethyl]methane [hereinafter called compound (1)] is provided comprising grained alpha-form crystals having improved coloration. The present invention further relates to a process for the production of compound (1), by transesterifying low-alkyl 3-(3,5-di-t-butyl-4-hydroxyphenyl)propionate [hereinafter called compound (2)] with pentaerythritol in the presence of a catalyst and aliphatic hydrocarbons as reaction solvent.

Exemplary aliphatic hydrocarbons include octane, isooctane, nonane, isononane, decane, isodecane, undecane, dodecane, tridecane, tetradecane, hexadecane, cyclooctane, and their mixtures. The aliphatic hydrocarbons to be used in this invention may contain small amounts of aromatic hydrocarbons such as cumene, pseudocumene, xylene, and ethyltoluene. The content of these aromatics in the above aliphatic hydrocarbons is preferred to be lower than 20%. The higher content of aromatics lowers the aniline point of the aliphatic hydrocarbons, which may cause the transesterification reaction to be slow.

The amount of aliphatic hydrocarbons as reaction solvent of this invention, which may be varied widely, is used in the range between 20 and 300 wt %, preferably between 50 and 200 wt %, on the basis of theoretical yield of compound (1); and as crystallization solvent in the range between 50 and 400 wt %, preferably between 100 and 200 wt %.

Exemplary ester-exchange catalysts include alkali metals such as sodium and lithium; alkali metal hydrides such as sodium hydride and lithium hydride; alkali metal amides such as lithium amide and sodium amide; and organo-tin compounds such as dibutyltin oxide, monooctyltin oxide, dioctyltin oxide, dibutyltin chloride and dioctyltin acetate. The most effective catalyst among the above is organo-tin compounds. These catalysts can be used in known quantity. The catalysts after reaction may be removed by washing and/or treatment with acids. Although aliphatic hydrocarbon may be added at the start of reaction if pentaerythritol has been pulverized, the solvent can be added after a short time reaction without the said solvent. In this case, it is recommended to add the reaction solvent immediately after the pentaerythritol has partly reacted with compound (2) to give a clear solution. The prolonged reaction time in the absence of the aliphatic hydrocarbon solvent causes an increased formation of colored by-products. The preferred molar ratio of pentaerythritol to compound (2) is in the range between 1:4.1 and 1:4.5.

After completion of the transesterification reaction of this invention using aliphatic hydrocarbons with the boiling point of 100° to 300° C., the compound (1) is crystallized preferably from the same solvent as the above reaction solvent. In this case, the compound (1) is obtained in the form of white grains having the melting point of 120° to 123° C. The shape of the compound (1) obtained is dependent mainly upon the kind of solvent used as crystallization solvent; that is, polar solvents such as lower alkyl alcohols like methanol and ethanol give fluffy crystals and nonpolar solvents such as aliphatic hydrocarbons give grain-shaped crystals. The grain size depends greatly upon the crystallization conditions; for example, milder conditions such as slow stirring and slow cooling give larger crystals in size although too slow is not economical.

The transesterification process of the present invention is applicable to the other forms of crystals such as beta-form, gamma-form, delta-form and lambda-form to improve their coloration.

Following Examples are illustrative.

EXAMPLE 1

27.2 g of powdered pentaerythritol and 237.0 g of methyl 3-(3,5-di-t-butyl-4-hydroxyphenyl)propionate and 0.2 g of lithium amide and 370 g of ISOPAR H (b.p. 176° to 189° C.; EXXON CHEMICAL AUSTRALIA LTD) were mixed and heated to 160° C. with stirring, in a 4-necked flask (1000 ml) equipped with a stirrer, a fractionating column, a thermometer and a nitrogen gas inlet. At temperatures between about 160° and 190° C., the reaction mixture was stirred with removal of the formed methanol, for a period of time of 14 hours until no more methanol went out.

The reaction mixture was cooled to 100° C. and 1.0 g of glacial acetic acid was added. The mixture was, after 30 minute agitation, filtrated to give 564 g of yellow and transparent solution. HPLC analysis indicated that the reaction rate[*1] was 98%.

(*1: The reaction rate is shown as the ratio of tetraester/(triester plus tetraester), which is calculated by integration of peaks of HPLC chart.)

The above filtrate was gradually cooled to 20° C. with slow stirring to crystallize the product. The crystals were collected by filtration and washed with cold heptane and dried under reduced pressure to give the product in the form of white and grained crystals. The yield and analytical data of the product are shown in Table 1.

EXAMPLE 2

The transesterification reaction was completed in the same manner as that of EXAMPLE 1 except that 1.0 g of dibutyltin oxide was used in place of lithium amide. The reaction rate was 99.0%. The reaction mixture was cooled to 110° C. and 1.0 g of oxalic acid was added. The mixture was, after 1 hour agitation at a temperature of 100° to 110° C., filtrated to give 560 g of pale yellow and transparent solution. The weight of the filtrate was made to 564g by the addition of 4 g of ISOPAR H. The product was crystallized in the same manner as that of EXAMPLE 1, filtered off at 20° C., washed with cold heptane, and dried under reduced pressure to give white and grained crystals. The yield and analytical data are shown in Table 1.

EXAMPLE 3

27.2 g of crystalline pentaerythritol and 237.0 g of methyl 3-(3,5-di-t-butyl-4-hydroxyphenyl)propionate and 1.0 g of dibutyltin oxide were mixed and heated to 170° C. with stirring, in the same flask as that of EXAMPLE 1. At temperatures between 170° and 190° C., the mixture was stirred for 2 hours with removal of the formed methanol. Into the clear reaction mixture, 370 g of ISOPAR H was added. The mixture was stirred for 8 hours at a temperature of 160° to 190° C. with removal of the formed methanol until no more methanol went out.

The product was obtained in the form of white and grained crystals, in the same manner as that of EXAMPLE 1. The reaction rate was 99.5% and the weight of the solution before crystallization was adjusted to 654 g. The yield and analytical data are shown in Table 1.

EXAMPLE 4

The product was obtained in the form of white and grained crystals, in the same manner as that of EXAMPLE 3 except that ISOPAR G (b.p. 155° to 175° C.; EXXON CHEMICAL AUSTRALIA LTD) was used in place of ISOPAR H.

The reaction rate was 99.6% and the weight of the solution before crystallization was adjusted to 564 g. The yield and analytical data are shown in Table 1.

EXAMPLE 5

The product was obtained in the form of white and grained crystals, in the same manner as that of EXAMPLE 3 except that IP-1620 (b.p. 166° to 205° C.; IDEMITSU PETROCHEMICAL CO., LTD, Japan) was used in place of ISOPAR H.

The reaction rate was 99.3% and the weight of the solution before crystallization was adjusted to 564 g. The yield and analytical data are shown in Table 1.

EXAMPLE 6

The product was obtained in the form of white and grained crystals, in the same manner as that of EXAMPLE 3 except that dioctyltin oxide is used in place of dibutyltin oxide.

The reaction rate was 99.7% and the weight of the solution before crystallization was 518 g. The yield and analytical data are shown in Table 1.

EXAMPLE 7

The product was obtained in the form of white and grained crystals, in the same manner as that of EXAMPLE 3 except that dibutyltin acetate is used in place of dibutyltin oxide.

The reaction rate was 99.5% and the weight of the solution before crystallization was adjusted to 518 g. The yield and analytical data are shown in Table 1.

COMPARATIVE EXAMPLE 1

27.2 g of powdered pentaerythritol and 237.0 g of methyl 3-(3,5-di-t-butyl-4-hydroxyphenyl)propionate and 0.2 g of lithium amide and 8.0 g of tetraline were mixed and heated to 130° C. with stirring, in a 4-necked flask (1000 ml) equipped with a stirrer, a condenser, a thermometer and a nitrogen inlet. At a temperature between 130° and 140° C., the mixture was stirred for 4 hours with removal of the formed methanol under reduced pressure (5 to 6 mmHg), and at a temperature between 150° and 160° C. for 10 hours under reduced pressure (2 to 3 mmHg). The reaction was completed by the distillation of small amounts of methanol generated and tetraline. The reaction rate was 97.0%.

The reaction mixture was cooled to 110° C. and the pressure was adjusted to atmospheric by introducing nitrogen gas. After addition of 250 ml of toluene and 1.0 g of glacial acetic acid to neutralize the mixture, the mixture was washed with 50 ml of distilled water twice, dried and filtrated. The yellow filtrate was stripped at a temperature of 150° C. under reduced pressure (0.5 mmHg) to isolate 245 g of product in the form of redish yellow glass.

COMPARATIVE EXAMPLE 2

50 g of the product obtained in COMPARATIVE EXAMPLE 1 was recrystallized from 75 g of ethanol to give the product in the form of white powder.

The yield and analytical data are shown in Table 1.

COMPARATIVE EXAMPLE 3

50 g of the product obtained in COMPARATIVE EXAMPLE 1 was recrystallized from 75 g of heptane to give the product in the form of yellow granular crystals.

The yield and analytical data are shown in Table 1.

COMPARATIVE EXAMPLE 4

50 g of the product obtained in COMPARATIVE EXAMPLE 1 was recrystallized from 75 g of ISOPAR G to give the product in the form of yellow granular crystals.

The yield and analytical data are shown in Table 1.

COMPARATIVE EXAMPLE 5

27.2 g of powdered pentaerythritol and 237.0 g of methyl 3-(3,5-di-t-butyl-4-hydroxyphenyl)propionate and 1.0 g of dibutyltin oxide and 370g of SOLVESSO 100 (an aromatic hydrocarbon: b.p., 160° to 175° C.; EXXON CHEMICAL AUSTRALIA LTD) were mixed and heated to 160° C., in the same flask as that of Example 1. The reaction mixture was stirred at a temperature of 160° to 175° C. for 12 hours with removal of the formed methanol in the same way as EXAMPLE 1. The reaction rate was, however, 63% and then the reaction was continued for additional 10 hours, but the reaction rate was still 69%.

An attempt of crystallization in the same manner as that of Example 1 has failed.

TABLE 1

| Example No. | Yield[2] (%) | Crystal shape | Melting Point (°C.) | Transmittance[3] 425 nm (%) | Transmittance[3] 500 nm (%) |
|---|---|---|---|---|---|
| Comparative Example 1 | 104 | glass | 50–60 | 65 | 75 |
| Comparative Example 2 | 77 | powder | 113–123 | 90 | 94 |
| Comparative Example 3 | 82 | granule | 120–123 | 73 | 82 |
| Comparative Example 4 | 85 | granule | 120–123 | 75 | 85 |
| Comparative Example 5 | — | — | — | — | — |
| Comparative Example 6[4] | — | powder containing grains | 113–115 | 91 | 95 |
| Example 1 | 89 | grain | 120–123 | 92 | 95 |
| Example 2 | 92 | grain | 121–123 | 96 | 97 |
| Example 3 | 93 | grain | 121–123 | 97 | 98 |
| Example 4 | 93 | grain | 121–123 | 98 | 99 |
| Example 5 | 94 | grain | 121–123 | 97 | 98 |
| Example 6 | 96 | grain | 121–123 | 98 | 99 |
| Example 7 | 95 | grain | 121–123 | 98 | 99 |

[2]The yield was calculated on the basis of moles of pentaerythritol used
[3]10 g of product was dissolved in 100 ml of toluene and transmittance of the above solution was measured. This method is usually used to indicate the degree of coloration; and the depth of yellow and/or red color is smaller as the figure of transmittance is higher.
[4]Irganox 1010

The improvement in coloration of compound (1) obtained in the grained crystals according to the process of the present invention is evident, as compared with Comparative Examples. As shown in Table 1, the crystals obtained in Examples have the melting point of 120° to 123° C., showing that the compound (1) prepared in accordance with this invention has a crystal structure of alpha-form. On the other hand, the found melting point (113° to 115° C.) of the commercial product indicates that it has a crystal structure of beta-form.

What is claimed is:

1. A process for the production of tetrakis [3-(3,5-di-t-butyl-4-hydroxyphenyl) propionyloxymethyl] methane in the form of alpha-form colorless crystals, by reacting pentaerythritol with lower-alkyl 3-(3,5-di-t-butyl-4-hydroxyphenyl)propionates in the presence of a catalyst and aliphatic hydrocarbons having a boiling point of from 100° C. to 300° C. as reaction solvent wherein the formed alcohol is removed by fractionation using a fractionating column, followed by crystallization from said aliphatic hydrocarbon and wherein the amount of aliphatic hydrocarbons as reaction solvent is in the range between 20 and 300 wt %, on the basis of theoretical yield of product and as crystallization solvent in the range between 50 and 400 wt %, on the basis of theoretical yield of product and wherein the product is crystallized from the solvent present during the reaction.

2. A process according to claim 1 in which the catalyst is organo-tin compounds.

3. A process according to claim 1 in which the catalyst is dibutyltin oxide.

4. A process according to claim 1 in which the catalyst is dioctyltin oxide.

5. A process according to claim 1 in which the catalyst is dibutyltin acetate.

6. A process according to claim 1 in which the aliphatic hydrocarbon is a mixture of aliphatic hydrocarbons having the boiling point from 155° to 205° C.

7. A process for the production of tetrakis [3-(3,5-di-t-butyl-4-hydroxyphenyl) propionyloxymethyl] methane in the form of alpha-form colorless crystals having a melting point of 120° C. to 123° C., comprising reacting pentaerythritol with the methyl ester of 3-(3-5-di-5-butyl-4-hydroxyphenyl)propionic acid at essentially atmospheric pressure in the presence of a transesterification catalyst and in the presence of aliphatic hydrocarbons as a reaction solvent, said hydrocarbons having a boiling point of from 100° C. to 300° C. wherein the formed methanol is removed by fractionation through a fractionating column and wherein the amount of aliphatic hydrocarbons as reaction solvent is in the range between 20 and 300 wt %, on the basis of theoretical yield and as crystallization solvent in the range between 40 and 400 wt %, the basis of theoretical yield of product and wherein the product is crystallized from the solvent present during the reaction.

8. The process of claim 7 wherein the catalyst is an organotin compound.

9. The process of claim 8 wherein the organotin compound is selected from the group consisting of dibutyltin oxide dioctyltin oxide and dioctyltin acetate.

10. Tetrakis [3-(3,5-di-t-butyl-4-hydroxyphenyl) propionyloxymethyl] methane in the form of alpha-form crystal grains having a melting point of 120° C. to 125° C., having a transmittance of more than 91 percent at 425 mm and more than 95 percent at 500 mm as measured as a solution of 10 grams in 100 ml of toluene in a standard 1 cm cell.

11. Tetrakis [3-(3,5-di-t-butyl-4-hydroxyphenyl) propionyloxymethyl] methane in the form of grained alpha-form crystal having a melting point of 120° C. to 123° C. and a transmittance of more than 91% at 425 mm and more than 95% at 500 mm as measured as a solution of 10 grams of 100 ml of toluene in a standard 1 cm cell.

12. Tetrakis [3-(3,5-di-t-butyl-4-hydroxyphenyl) propionyloxymethyl] methane in the form of alpha-form crystal grains, having a melting point of 121° C. to 123° C., having a transmittance of more than 91 percent at 425 mm and more than 95 percent at 500 mm as measured as a solution of 10 grams in 100 ml of toluene in a standard 1 cm cell.

* * * * *